United States Patent [19]
Akito et al.

[11] 4,073,931
[45] Feb. 14, 1978

[54] NITROGLYCERINE INCLUSION COMPOUNDS WITH CYCLODEXTRIN AND COMPOSITION CONTAINING SAME

[75] Inventors: Eiichiro Akito, Omiya; Yoshiyuki Nakajima, Chiba; Masayoshi Horioka, Fukuoka, all of Japan

[73] Assignees: Teijin Limited, Osaka; Nippon Kayaku Kabushiki Kaisha, Tokyo, both of Japan

[21] Appl. No.: 561,884

[22] Filed: Mar. 25, 1975

[30] Foreign Application Priority Data

Mar. 27, 1974 Japan .................................. 49-34176

[51] Int. Cl.$^2$ ........................ A61K 9/20; C08B 37/16
[52] U.S. Cl. ................................... 424/298; 424/361; 536/46; 536/103
[58] Field of Search ....................... 260/209 R, 209 D; 424/16, 361, 180, 298; 536/46, 103

[56] References Cited

U.S. PATENT DOCUMENTS

| 3,061,444 | 10/1962 | Rogers et al. | 260/209 D |
| 3,627,583 | 12/1971 | Troy | 424/361 |
| 3,789,119 | 1/1974 | Fusari et al. | 424/361 |

Primary Examiner—Johnnie R. Brown
Attorney, Agent, or Firm—Schuyler, Birch, Swindler, McKie & Beckett

[57] ABSTRACT

Nitroglycerine inclusion compound in cyclodextrin is obtained by contacting cyclodextrin with nitroglycerine in the presence of water. The inclusion compound is very stable as a quick effective drug for treating angina pectoris and easy in handling.

5 Claims, 6 Drawing Figures

NITROGLYCERINE INCLUSION COMPOUNDS WITH CYCLODEXTRIN AND COMPOSITION CONTAINING SAME

The present invention relates to an inclusion compound of nitroglycerine in cyclodextrin and a process for producing the same. More particularly, the present invention relates to a method for providing a nitroglycerine having a low volatility by contacting nitroglycerine with cyclodextrin in the presence of water to form an inclusion compound of nitroglycerine in cyclodextrin thereby improving the volatility, which is a defect of nitroglycerine.

Since it was reported by Wegria in 1951 that nitroglycerine has the same smooth muscle relaxing action and the peripheral vasodilating action as the nitrite ester [refer to American Journal of Medicine 10, 414, (1951)], the sublingual tablets thereof have most widely been used as a useful and quick effective remedy for the attack of angina pectoris by its vasodilating action on the coronary vessels and other peripheral blood vessels.

The nitroglycerine-containing tablets, however, strongly tend to decrease in nitroglycerine content due to gradual volatilization of nitroglycerine because of the strong volatility of the main ingredient, nitroglycerine, and therefore, nitroglycerine tablets frequently have not shown the expected effect when used in the treatment of attack of angina pectoris.

Development of nitroglycerine tablets having low volatility has, therefore, been a very important problem for those skilled in the art.

In order to solve the problem, heretofore, a method comprising adsorbing nitroglycerine onto the micro-crystalline cellulose has been proposed [M. David Richman et al., Journal of Pharmaceutical Science 54, 447 (1965)].

The sublingual tablets produced according to this method were, however, not satisfactory even though improvement in volatility was obtained as compared with the previous drugs. The sublingual tablets had also the defects of sensation of foreign body and uncomfortableness because of the insolubility of the micro-crystalline cellulose in water.

The nitroglycerine tablets are usually small tablets each weighing 30 mg and having a diameter of about 4 mm. They usually are stored in a small slender glass tube having a tight rubber stopper in order to prevent the reduction of the nitroglycerine content as much as possible. Consequently, it has been difficult to take out one tablet from the tube in case of an emergency attack of angina pectoris. Consequently, it has been desired to provide a drug capable of being stored in such a package form as a strip-package.

As a result of intensive research investigation to prevent such volatility of nitroglycerine, the present inventors have found that, when nitroglycerine is included in cyclodextrin, an inclusion compound of nitroglycerine in cyclodextrin can easily be produced which is capable of preventing the volatility of nitroglycerine and which loses very small amount of nitroglycerine content during storage and which can be made even into a powder and that the thusly obtained inclusion compound is very high in storage stability and easy in handling and that it is also stable in tablet-forming and the like. The present invention has been accomplished based upon this finding.

An object of the present invention is to provide a nitroglycerine inclusion compound as a remedy for treating angina pectoris which is stable during storage and easy in handling.

Another object of the present invention is to provide a process for producing a nitroglycerine inclusion compound in cyclodextrin which comprises contacting nitroglycerine with cyclodextrin in the presence of water.

Further objects and advantages of the present invention will become apparent from the following description.

Cyclodextrin used in the present invention is also called by the name of Schardinger-dextrin. It is a compound having a cyclic structure and having 6 to 8 or more D-glucose units connected through an α-1,4-glycoside linkage. The cyclodextrins having D-glucose units comprising 6, 7 and 8 molecules are called as α-cyclodextrin, β-cyclodextrin and γ-cyclodextrin, respectively. These cyclodextrins are obtained by subjecting starch or dextrin to the reaction with specific enzymes and they show excellent solubility in water. The solubility of β-cyclodextrin in water is, for example, as shown in Table 1.

Table 1

| Temperature (° C) | Solubility (g/100 ml) |
|---|---|
| 20 | 1.8 |
| 40 | 3.7 |
| 60 | 8.0 |
| 80 | 18.3 |
| 100 | 25.6 |

The process of the present invention is carried out by contacting nitroglycerine with cyclodextrin having such properties in the presence of water, preferably, in the following manner.

One part by weight of cyclodextrin is admixed with 2 to 100 parts, preferably 5 to 70 parts, by weight of water to form a pasty or suspension mixture and treated to form a saturated aqueous solution by heating at 40° to 100° C. if necessary. To this mixture is added gradually with stirring 0.001 to 0.2 part by weight of nitroglycerine in solution in a hydrophilic organic solvent such as, for example, methanol, ethanol, acetone and the like. Blending is continued for 4 to 8 hours after which the mixture is allowed to stand until cool.

In this case, the amount of cyclodextrin and water used as well as the heating temperature can be selected suitably by taking the solubility of cyclodextrin into consideration. As mentioned above, cyclodextrin need not necessarily be dissolved in water completely but it is preferable to dissolve it in water completely for easy handling.

The inclusion compound of nitroglycerine in cyclodextrin may be precipitated by allowing the mixture to stand and may be separated from the mother liquor by means of filtration or centrifugation and the like. The inclusion compound thus obtained is washed with cold water or suitable organic solvents, if necessary, and then dried. The nitroglycerine content (% by weight) in the inclusion compound thus obtained can be determined by subjecting said inclusion compound to extraction treatment with chloroform to extract nitroglycerine in the chloroform and subjecting the extract to gas-chromatography.

The fact that the material obtained in such manner as mentioned above is the inclusion compound of nitroglycerine in cyclodextrin was confirmed, as mentioned later, by X-ray powder patterns and differential thermal analysis (refer to Experimental Example 1). The inclusion compound may be used as such in the powder form or it may be admixed with fine particles comprising a suitable combination of requirement amount of excipients such as lactose, corn starch, mannitol, or micro-crystalline cellulose and binders such as polyvinylpyrrolidone, gum arabic, starch paste or methylcellulose and further with lubricants such as magnesium stearate or talc and the mixture is formed into tablets. Thus, the inclusion compound is used in the tablet form.

Further, a therapeutically effective dosage range for the inclusion compound of the present invention is usually 1 to 600 mg per one dosage for an adult.

The inclusion compound obtained in accordance with the process of the present invention can be used not only in pharmaceuticals as mentioned above, but also in explosive materials having novel properties utilizing the stability thereof.

The process of the present invention is illustrated in detail by reference to Examples hereinbelow, but the present invention is not limited at all by these Examples.

EXAMPLE 1

A mixture of 20 g of $\beta$-cyclodextrin and 150 ml of water was heated at 80° C to make a solution. To the resulting solution was added dropwise gradually 2 g of nitroglycerine in very small portions under stirring over 15 minutes. After completion of addition, the mixture was further stirred for about an hour and then allowed to stand for about 4 hours to precipitate the white inclusion compound. The inclusion compound was filtered and dried to obtain 18.5 g of powdery product. The nitroglycerine content of the product was 9.3% by weight as determined by subjecting to gas-chromatography after extraction treatment with chloroform.

EXAMPLE 2

A mixture of 40 g of $\beta$-cyclodextrin and 800 ml of water was heated at 50° C to make a solution. To the resulting solution was added gradually a solution of 3 g of nitroglycerine in 30 ml of ethanol with stirring over 20 minutes.

The mixture was then treated in the same manner as in Example 1 to give 31.5 g of the powdery product having a nitroglycerine content of 8.2% by weight.

EXAMPLE 3

A mixture of 40 g of $\beta$-cyclodextrin and 600 ml of water was heated at 80° C to make a solution. To this solution was added gradually a solution of 6 g of nitroglycerine in 12 ml of acetone with stirring over 15 minutes.

The mixture was then treated in the same manner as in Example 1 to give 36 g of the powdery product having a nitroglycerine content of 14.8% by weight.

In order to confirm whether or not the product obtained in accordance with the process of the present invention was an inclusion compound in cyclodextrin, the following experiment was carried out.

Experimental Example 1

Figure 1:
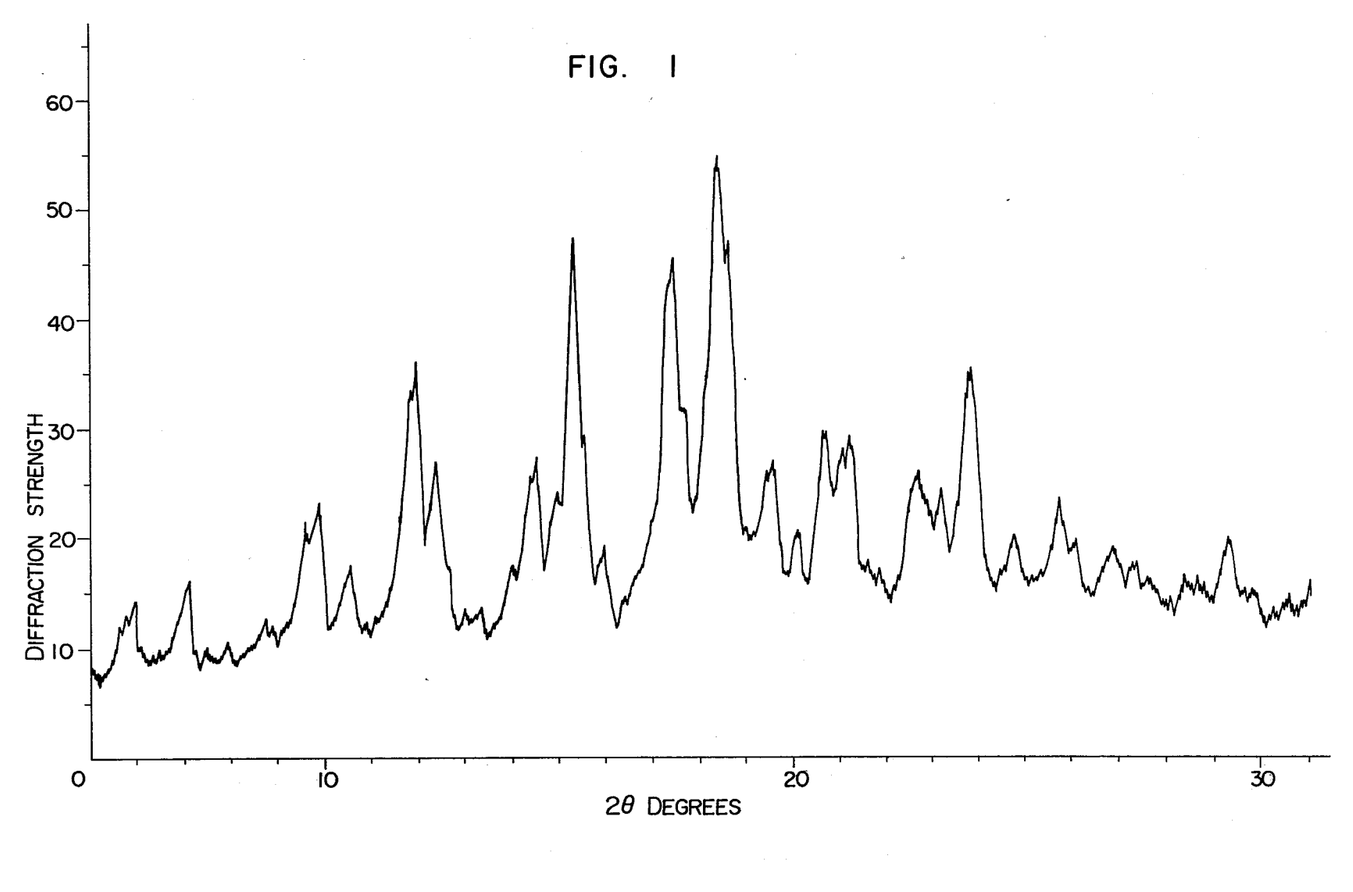
Figure 2:
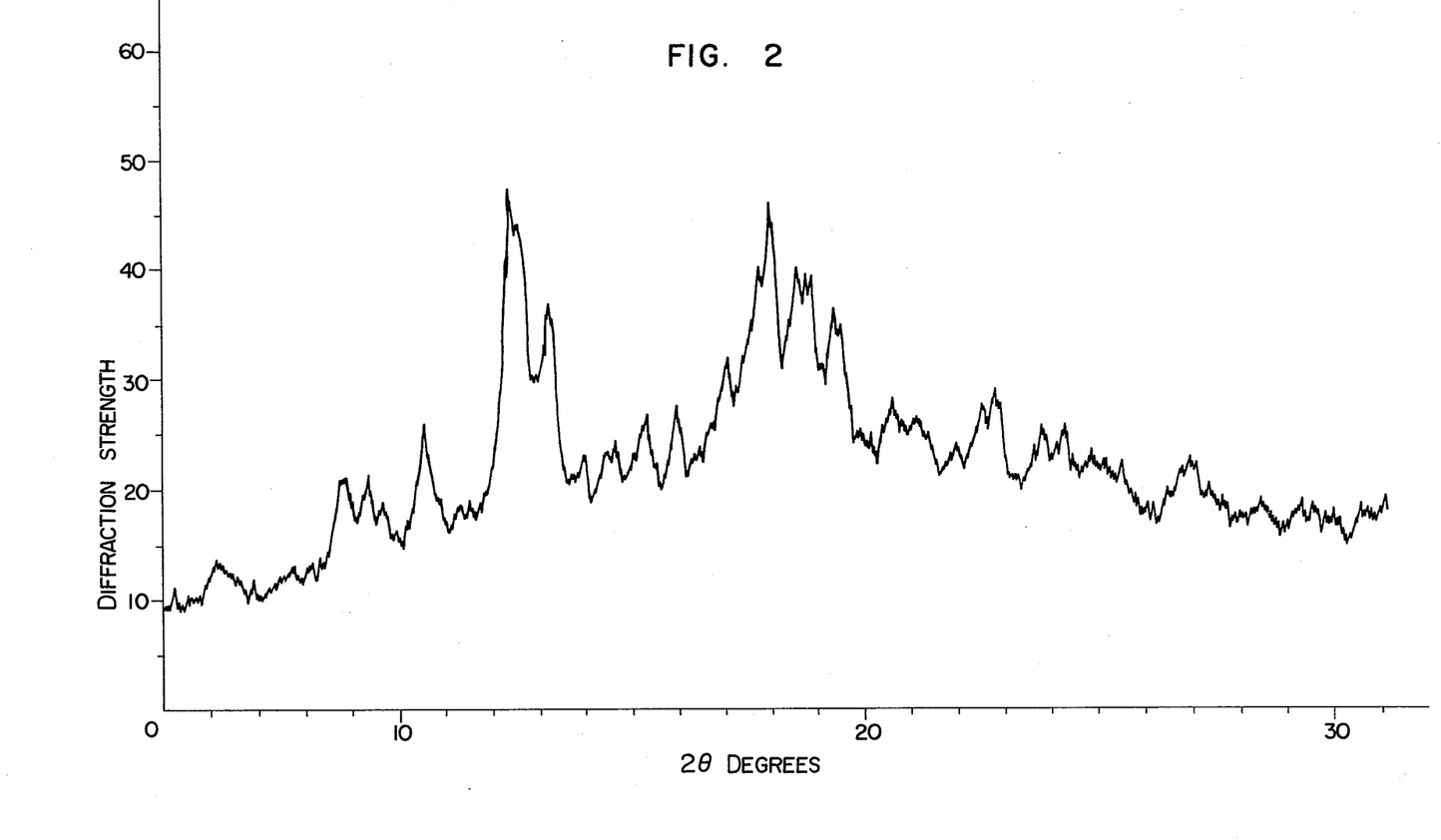
Figure 3:
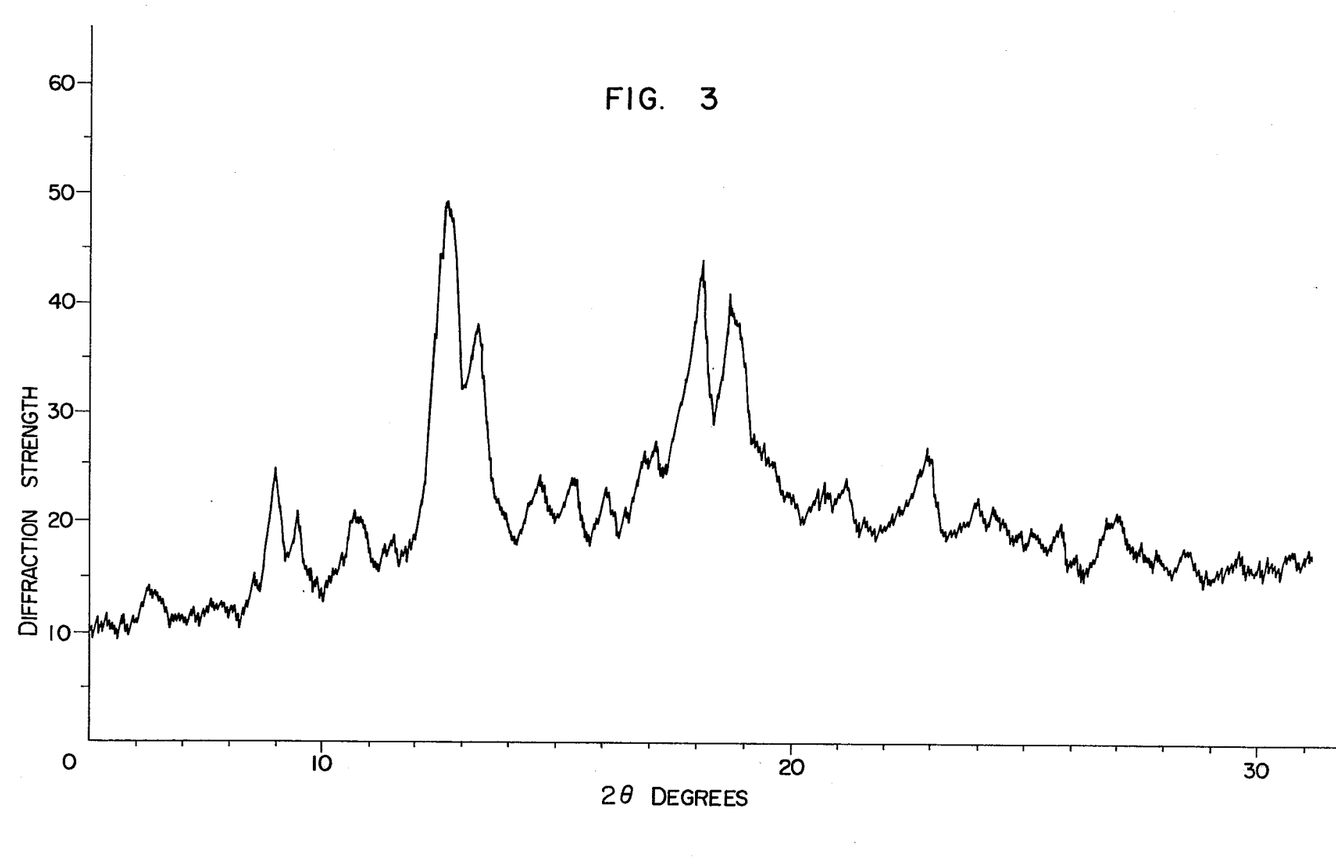

1. X-Ray powder patterns:
1. Sample
(i) Product obtained in Example 1 (nitroglycerine content: 9.3%); 300 mg
(ii) A mixture of $\beta$-cyclodextrin and nitroglycerine (nitroglycerine content: 9.3%); 300 mg
(iii) $\beta$-Cyclodextrin; 300 mg 2. Experimental method
A D-8C type X-ray diffraction apparatus manufactured by Rigaku Denki Co., Ltd. was used: The experiment was carried out according to the powder X-ray diffraction method using Ni filtered copper K$\alpha$-radiation, 30 KV, 10 mA, detector; GMC, 1° divirgency, receiving slits 0.15 mm, scanning speed 20°/min.
3. Results
FIG. 1 shows a X-ray powder pattern of the product obtained in Example 1, and FIG. 2 shows that of a mixture of $\beta$-cyclodextrin and nitroglycerine and FIG. 3 shows that of $\beta$-cyclodextrin.

As is evident from these drawings, there was almost no difference between the diffraction peaks at $2\theta$ of a mixture of $\beta$-cyclodextrin and nitroglycerine (FIG. 2) and of $\beta$-cyclodextrin (FIG. 3) and there was no change in the crystalline lattice of $\beta$-cyclodextrin, whereas there was an deformation in the diffraction peak of the product obtained in accordance with the present invention (FIG. 1) as compared with the cases of Samples (ii) and (iii), showing a change in the crystalline lattice of $\beta$-cyclodextrin.

Figure 4:
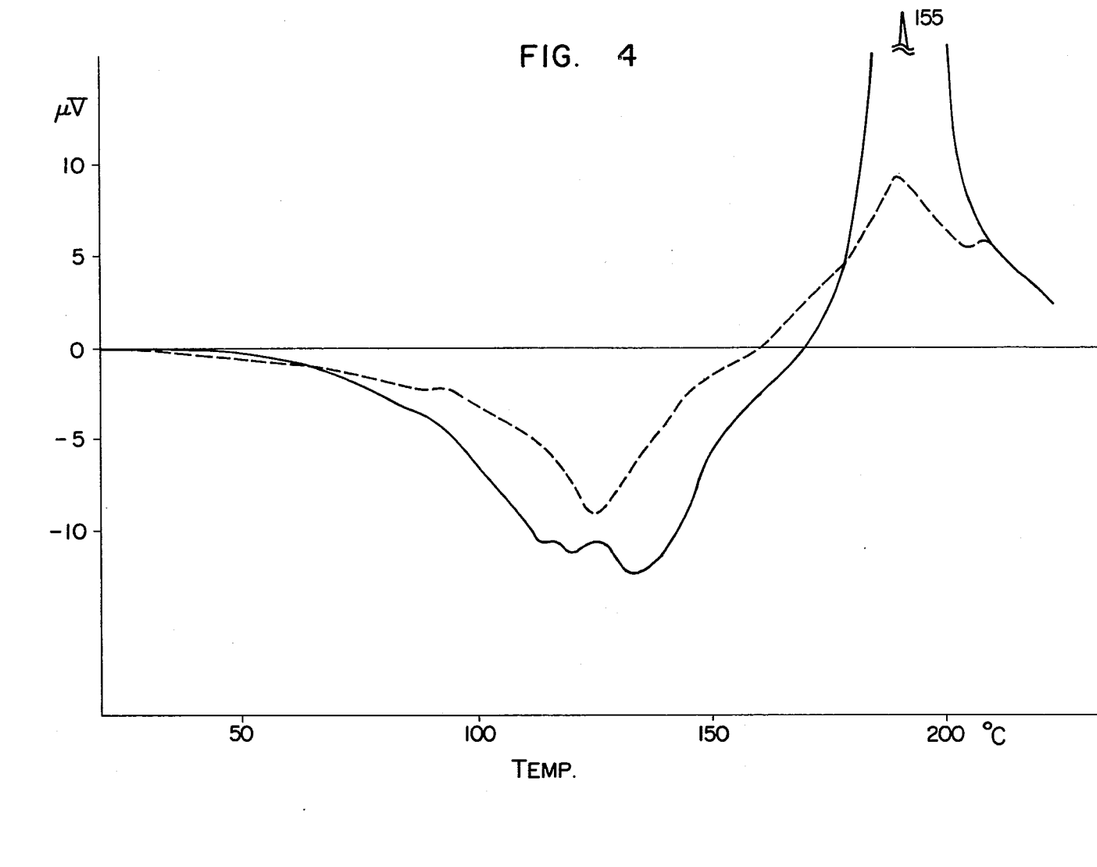

2. Differential thermal analysis:
1. Sample
(i) Product obtained in Example 1 (nitroglycerine content: 9.3%)
(ii) A mixture of $\beta$-cyclodextrin and nitroglycerine (nitroglycerine content: 9.3%)
2. Experimental method
Differential heat was determined at a temperature from 20° to 250° C at heating rate of 10° C/min. using the differential heat balance, type MTG-11 manufactured by Shimazu Co.
3. Results
FIG. 4 is a determination chart of the differential heat. In the drawing, the solid line shows the thermogram of the product obtained in Example 1 and the dotted line show the thermogram of a mixture of $\beta$-cyclodextrin and nitroglycerine. As is evident from this drawing, the product obtained in accordance with the present invention includes nitroglycerine until it reaches the decomposition temperature of nitroglycerine and hence it causes a large exothermic reaction at 192° C, while most of nitroglycerine evaporates before decomposition of nitroglycerine in the mixture of $\beta$-cyclodextrin and nitroglycerine and, therefore, the heat evolution at the decomposition temperature of nitroglycerine is very small.

From the result of the above experiment, it can be said that the product obtained in accordance with the process of the present invention forms an inclusion compound of nitroglycerine in $\beta$-cyclodextrin.

Experiments carried out on the volatility of the powder of an inclusion compound of nitroglycerine in cyclodextrin obtained in accordance with the present invention and that of the nitroglycerine-containing powder prepared by the conventional method and the micro-crystalline cellulose method are described hereinbelow.

Experimental Example 2 (Tests with powder)

1. Sample
(i) The powdery product obtained in accordance with the process of the present invention: The powdery product obtained in Example 3 was used.
(ii) Conventional product (for comparison): A lactose granule pelletized by the use of gum arabic as a binder was sprayed with a 3% ethanolic solution of nitroglycerine with stirring, blending homogeneously and dried. The resulting mixture was ground in a mortar and used.

2. Experimental method

About 1 g of each sample was weighed accurately in an open weighing bottle and maintained at a temperature of 30° C, and a pressure of 5 mm Hg. Samples were taken out at certain intervals and extracted with chloroform, and the extract was subjected to gas-chromatography to determine the nitroglycerine content.

3. Results

The results obtained are shown in Table 2. In the Table, the evaporation rate (%) represents the rate of evaporation (%) of nitroglycerine with the lapse of time against the initial nitroglycerine content of 100% in the sample at the maintenance time 0.

Table 2

| Sample Maintenance time | Product of the present process | | Product of the conventional process | |
|---|---|---|---|---|
| | Content (%) | Evaporation rate (%) | Content (%) | Evaporation rate (%) |
| 0 | 14.8 | — | 1.32 | — |
| 2.0 | 14.1 | 4.7 | 0.93 | 29.5 |
| 4.0 | 13.9 | 6.1 | 0.92 | 30.3 |
| 6.0 | 13.8 | 6.8 | 0.90 | 31.8 |
| 20.0 | 12.8 | 13.5 | 0.44 | 66.7 |

As is evident from the above table, although the initial content of nitroglycerine in the product of the present process is about 10 times as much as that of the product of the conventional process, the evaporation rate of nitroglycerine in the product of the present invention with the lapse of time is only about ¼ to 1/10 as much as that of the product of the conventional process, and it was recognized that the volatility thereof was improved markedly.

Experimental Example 3 (Tests with tablets)

1. Sample
(i) Tablets formed from the powdery product obtained by the process of the present invention: 2.05 g of the powdery product obtained in Example 1, fine particles prepared from 22.92 g of lactose, 4.58 g of corn starch and 0.3 g of polyvinylpyrrolidone, and 0.15 g of magnesium stearate were admixed and the mixture was formed into tablets each weighing 30 mg and having a diameter of 4 mm. Each tablet had a nitroglycerine content of 0.299 mg.
(ii) Conventional product (I): The granules of the conventional product prepared in the same manner as in Experimental Example 2 were formed into tablets each weighing 30 mg and having a diameter of 4 mm. Each tablet had a nitroglycerine content of 0.305 mg.
(iii) Conventional product (II) (Tablets prepared from micro-crystalline cellulose): a 20% acetone solution of nitroglycerine was sprayed over microcrystalline cellulose under agitation, admixed homogeneously and the mixture was dried. To this were added and admixed fine particles prepared from lactose, corn starch and polyvinylpyrrolidone, and the mixture was formed into tablets each weighing 30 mg and having a diameter of 4 mm. Each tablet had a nitroglycerine content of 0.296 mg.

2. Experimental method

Thirty tablets of each individual sample were placed in separate open Petri dishes ten centimeters in diameter so that no tablet overlapped any other and the dishes were kept in a ventilation type oven at 50° C. After 4 days, 10 tablets of individual samples were taken out and extracted with chloroform and the extract was subjected to gas-chromatography to determine the nitroglycerine content.

3. Results

The results obtained were shown in Table 3. In the table, the nitroglycerine content and evaporation rate were a mean value of 10 tablets, respectively.

Table 3

| Sample Maintenance days | Product of the present process | | Conventional product (I) | | Conventional product (II) | |
|---|---|---|---|---|---|---|
| | Nitroglycerine content (mg) | Evaporation rate (%) | Nitroglycerine content (mg) | Evaporation rate (%) | Nitroglycerine content (mg) | Evaporation rate (%) |
| 0 | 0.299 | — | 0.305 | — | 0.291 | — |
| 4 | 0.215 | 28 | 0.001 | 100 | 0.081 | 71 |
| 7 | 0.174 | 42 | — | — | 0.056 | 81 |

The following is evident from the above table. There is almost no difference between the initial nitroglycerine content in each sample. After 4 days, the conventional product (I) has already evaporated all of nitroglycerine contained therein and the conventional product (II) has also evaporated 81% of the initial nitroglycerine content, while the product of the present process has evaporated only 42% of the initial nitroglycerine content.

Experimental Example 4 (Test of the effects of sublingual administration of tablets)

1. Sample
(i) Product of the present process: tablets prepared in Experimental Example 3-(1)-(i)
(ii) Conventional product (I): tablets prepared in Experimental Example 3-(1)-(ii)
(iii) Placebo: A solution of 240 mg of Tinctra Capsici (Japanese Pharmacopoeia 8th, ed.) in ethanol was sprayed over 15 g of lactose granules and dried, and the product was then formed into tablets each weighing 30 mg and having a diameter of 4 mm. Tinctra Capsici was added to simulate the taste of nitroglycerine tablets.

2. Experimental method

One tablet of each of the above samples was given sublingually to 4 healthy adults and the maximum and minimum blood pressures, average blood pressure and heart rate were measured immediately before administration and in the time intervals up to 30 minutes after administration. The experiment was carried out for 4 days. The product of the present process was given two times and other products were given once, respectively, to each subject.

3. Results

Figure 5:
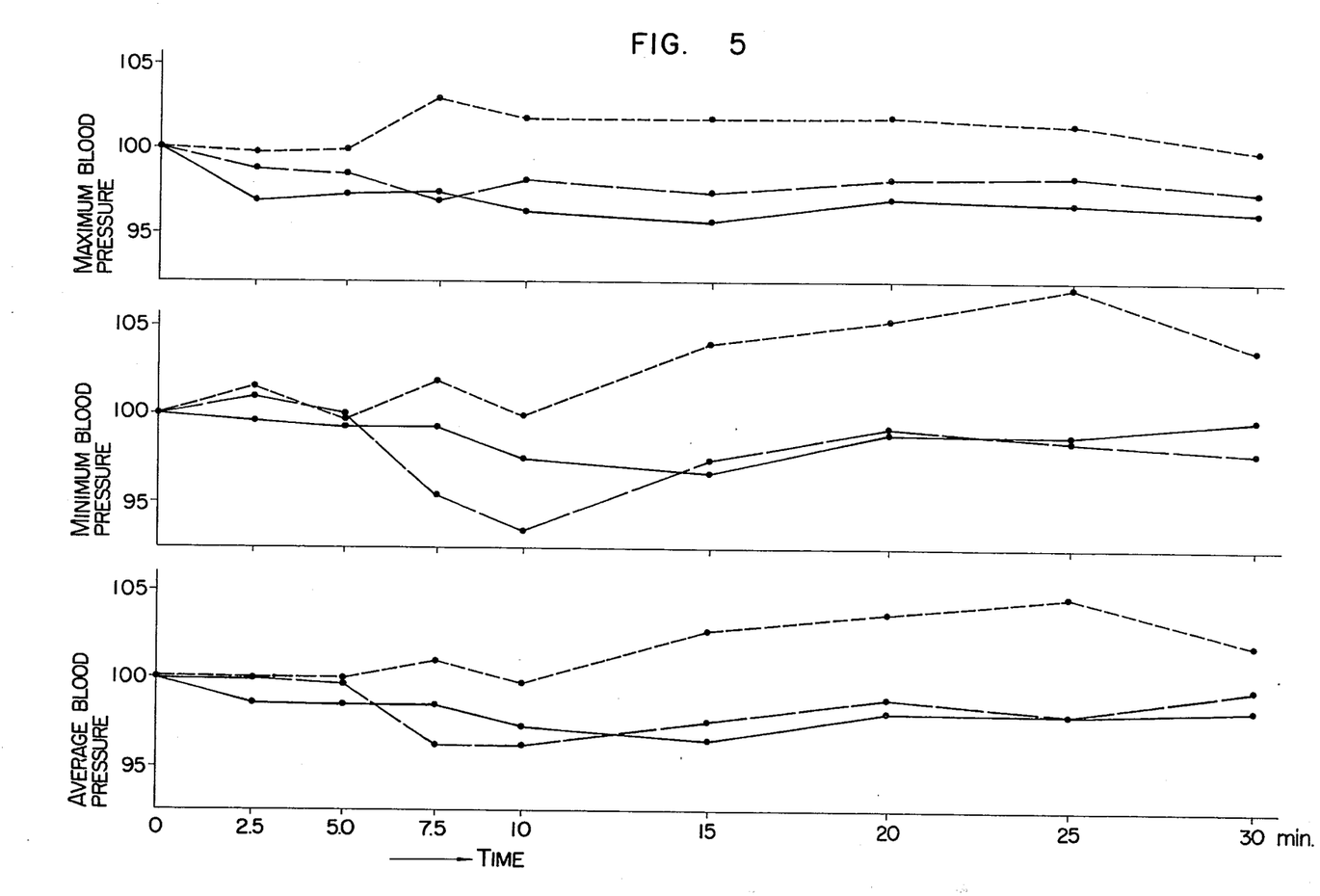
Figure 6:
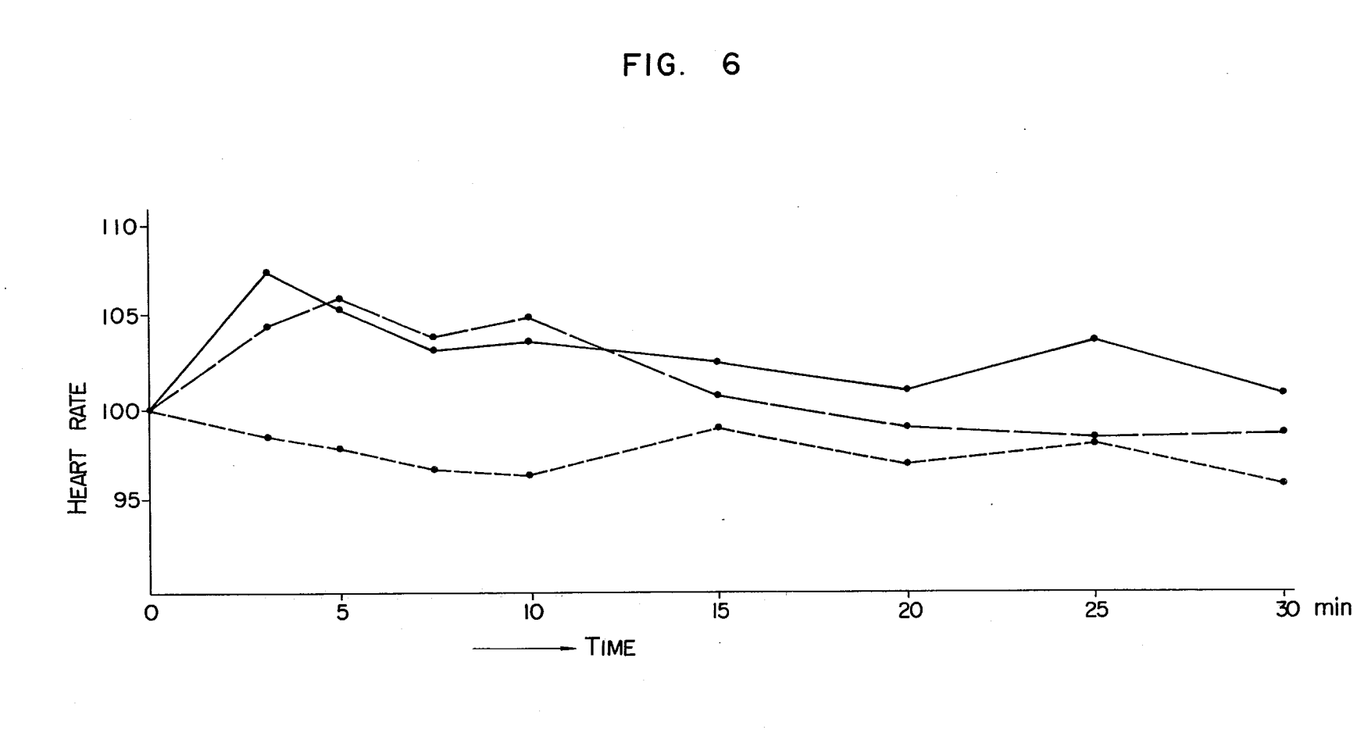

The results are shown in FIG. 5 and FIG. 6. FIG. 5 shows the change of the blood pressure with the lapse of time. The maximum blood pressure, minimum blood pressure and the average blood pressure immediately before administration was calculated as 100 and the respective values obtained at each of the time intervals after administration against the initial value were plotted. FIG. 6 shows the change of the heart rate with the lapse of time. The heart rate was plotted in the same manner as above. In FIGS. 5 and 6, the solid line represents the case of the present product, the broken line represents the case of the conventional product (I) and the dotted line represents the case of the placebo. As is evident from the two drawings, the product of the present process and the conventional product (I) show a greater effect than the placebo. In general, the product of the present process is slightly more effective than the conventional product (I).

As mentioned above, it is evident that an inclusion compound of nitroglycerine in cyclodextrin obtained in accordance with the present process has the least volatility of nitroglycerine. For example, the preparations containing said inclusion compound as well as most of other raw material are water-soluble and cause no sensation of foreign body or unpleasant sensation in the sublingual region. Since said inclusion compound has little volatility, there occurs almost no change in the content of nitroglycerine during the course of storage.

Hence, what is claimed is:

1. An inclusion compound of nitroglycerine in cyclodextrin.

2. A process for producing an inclusion compound of nitroglycerine in cyclodextrin which comprises contacting 0.2 to 0.001 part by weight of nitroglycerine with 1 part by weight of cyclodextrin in the presence of 5–70 parts by weight of water.

3. A process according to claim 2, wherein said nitroglycerine is dissolved in a hydrophilic organic solvent and then brought into contact with a mixture of cyclodextrin and water.

4. A process according to claim 3, wherein the hydrophilic organic solvent is at least one member selected from the group consisting of methanol, ethanol and acetone.

5. A pharmaceutical tablet comprising a blend of (1) an inclusion compound of nitroglycerine in cyclodextrin, and (2) tablet-forming fine particles comprising at least one excipient selected from the group consisting of lactose, corn starch, mannitol and fine crystalline cellulose; said particles further comprising at least one binder selected from the group consisting of polyvinylpyrrolidone, gum arabic and methyl cellulose.

* * * * *